United States Patent
Gura et al.

(10) Patent No.: US 7,892,196 B2
(45) Date of Patent: *Feb. 22, 2011

(54) WEARABLE CONTINUOUS RENAL REPLACEMENT THERAPY DEVICE

(75) Inventors: Victor Gura, Beverly Hills, CA (US); Edmond Rambod, Los Angeles, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 631 days.

This patent is subject to a terminal disclaimer.

(21) Appl. No.: 11/933,533

(22) Filed: Nov. 1, 2007

(65) Prior Publication Data

US 2008/0058696 A1 Mar. 6, 2008

Related U.S. Application Data

(63) Continuation of application No. 10/940,862, filed on Sep. 14, 2004, now Pat. No. 7,309,323, which is a continuation-in-part of application No. 10/085,349, filed on Nov. 16, 2001, now Pat. No. 6,960,179.

(51) Int. Cl.
*A61M 37/00* (2006.01)
*C02F 1/44* (2006.01)

(52) U.S. Cl. .............. 604/5.04; 210/646; 210/645; 210/739; 604/6.09; 604/6.11

(58) Field of Classification Search ............. 604/4.01, 604/5.01, 5.04, 6.09, 6.11, 29, 361, 358, 604/327; 210/645, 646, 739, 195.2, 433.1, 210/500.1; 422/44
See application file for complete search history.

(56) References Cited

U.S. PATENT DOCUMENTS

| | | | |
|---|---|---|---|
| 3,388,803 A | 6/1968 | Scott | |
| 3,746,175 A | 7/1973 | Markley | |
| 3,884,808 A | 5/1975 | Scott | |
| 3,902,490 A | 9/1975 | Jacobsen et al. | |
| 3,989,622 A | 11/1976 | Marantz et al. | |
| 3,994,799 A | 11/1976 | Yao et al. | |
| 4,094,775 A | 6/1978 | Mueller | |
| 4,209,392 A | 6/1980 | Wallace | |

(Continued)

FOREIGN PATENT DOCUMENTS

DE 20113789 U1 5/2002

OTHER PUBLICATIONS

Shettigar, et al, "A portable hemodialysis/hemofiltration system independent of dialysate and infusion fluid." Artif Organs, vol. 7, No. 2, May 1983, pp. 254-256.

(Continued)

*Primary Examiner*—Leslie Deak
(74) *Attorney, Agent, or Firm*—Hamilton, Brook, Smith & Reynolds, P.C.

(57) ABSTRACT

A continuous renal replacement therapy (CRRT) device adapted to be worn on a portion of the body of a patient. The CRRT device is worn by the patient and operates on rechargeable batteries for more than 5 hours. Dialysate is used to remove impurities from the blood. The dialysate is recycled and refreshed by a filter section. Less than one liter of dialysate is required to circulate through the wearable CRRT device.

20 Claims, 9 Drawing Sheets

U.S. PATENT DOCUMENTS

| | | | |
|---|---|---|---|
| 4,212,738 | A | 7/1980 | Henne |
| 4,247,393 | A | 1/1981 | Wallace |
| 4,267,040 | A | 5/1981 | Schal |
| 4,269,708 | A | 5/1981 | Bonomini et al. |
| 4,443,333 | A | 4/1984 | Mahurkar |
| 4,765,907 | A | 8/1988 | Scott |
| 4,897,189 | A | 1/1990 | Greenwood et al. |
| 4,968,422 | A | 11/1990 | Runge et al. |
| 4,997,570 | A | 3/1991 | Polaschegg |
| 5,284,470 | A | 2/1994 | Beltz |
| 5,284,559 | A | 2/1994 | Lim et al. |
| 5,415,532 | A | 5/1995 | Loughnane et al. |
| 5,577,891 | A | 11/1996 | Loughnane et al. |
| 5,725,776 | A | 3/1998 | Kenley et al. |
| 5,902,336 | A | 5/1999 | Mishkin |
| 5,910,252 | A * | 6/1999 | Truitt et al. ............... 210/645 |
| 5,944,684 | A | 8/1999 | Roberts et al. |
| 5,980,481 | A | 11/1999 | Gorsuch |
| 5,984,891 | A | 11/1999 | Keilman et al. |
| 6,117,100 | A | 9/2000 | Powers et al. |
| 6,117,122 | A | 9/2000 | Din et al. |
| 6,168,578 | B1 | 1/2001 | Diamond |
| 6,196,992 | B1 | 3/2001 | Keilman et al. |
| 6,325,774 | B1 | 12/2001 | Bene et al. |
| 6,332,985 | B1 | 12/2001 | Sherman et al. |
| 6,406,631 | B1 | 6/2002 | Collins et al. |
| 6,561,997 | B1 | 5/2003 | Weitzel et al. |
| 6,758,975 | B2 | 7/2004 | Peabody et al. |
| 6,776,912 | B2 | 8/2004 | Baurmeister |
| 6,796,955 | B2 | 9/2004 | O'Mahoney et al. |
| 6,843,779 | B1 | 1/2005 | Andrysiak et al. |
| 7,309,323 | B2 * | 12/2007 | Gura et al. ............... 604/5.04 |
| 2002/0112609 | A1 | 8/2002 | Wong |
| 2004/0133145 | A1 | 7/2004 | Bene |

OTHER PUBLICATIONS

Manns, Markus et al, "The acu-men: A New Device for Continuous Renal Replacement Therapy in Acute Renal Failure," Kidney International, vol. 54, 1998, pp. 268-274.

Lockridge, R.S. Jr., "The Direction of End-Stage Renal Disease Reimbursement in the United States," Semin Dial, vol. 17, 2004, pp. 125-130.

Lockridge, R.S. Jr., et al, "Is HCFA's Reimbursement Policy Controlling Quality of Care for End-State Renal Disease Patients?" ASAIO J, vol. 47, 2001, pp. 466-468.

Manns, B.J. et al, "Dialysis Adequacy and Health Related Quality of Life in Hemodialysis Patients," ASAIO J, vol. 48, 2002, pp. 565-569.

Mapes, D.L. et al, "Health-related Quality of Life as a Predictor of Mortality and Hospitalization: The Dialysis Outcomes and Practice Patterns Study (DOPPS)," Kidney Int., vol. 64, 2003, pp. 339-349.

McFarlane, P.A. et al, "The Quality of Life and Cost Utility of Home Nocturnal and Conventional In-center Hemodialysis," Kidney Int., vol. 64, 2003, pp. 1004-1011.

Mohr, P. E., et al, "The Case for Daily Dialysis: Its Impact on Costs and Quality of Life," Am J Kidney Dis., vol. 37, 2001, pp. 777-789.

Patel, S. S., et al, "Psychosocial Variables, Quality of Life, and Religious Beliefs in ESRD Patients Treated with Hemodialysis," Am J Kidney Dis., vol. 40, 2002, pp. 1013-1022.

"Sorbent Dialysis Primer," Organon Teknika Corp., 1991.

Ronco, C., et al, "Blood and Dialysate Flow Distribution in Hollow-fiber Hemodialyzers Analyzed by Computerized Helical Scanning Technique," J Am Soc Nephrol, vol. 13, 2002, pp. S53-S61.

Mineshima, M., et al, "Effects of Internal Filtration on the Solute Removal Efficiency of a Dialyzer." ASAIO J, vol. 46, 2000, pp. 456-460.

Ronco, C., et al, "The Hemodialysis System: Basic Mechanisms of Water And Solute Transport in Extracorporeal Renal Replacement Therapies," Nephrol Dial Transplant, vol. 13 Suppl. 6, 1998, pp. 3-9.

Miwa, M. et al, "Push/Pull Hemodiafiltration: Technical Aspects and Clinical Effectiveness," Artif Organs, vol. 23, 1999, pp. 1123-1128.

Runge, T.M., et al, "Hemodialysis: Evidence of Enhanced Molecular Clearance and Ultrafiltration Volume by Using Pulsatile Flow," Int J Artif Organs, vol. 16, 1993, pp. 645-652.

Ding, L. H., et al, "Dynamic filtration of Blood: A New Concept For Enhancing Plasma Filtration," Int J Artif Organs, vol. 14, 1991, pp. 365-370.

Bird, R. B., et al, Transport Phenomena, Wiley, New York, 1976, pp. 126-130, 502-531, 558-563, 624-625, 700-711.

Welty, J. R., et al, "Chapter 27: Unsteady-state Molecular Diffusion," Fundamentals of Momentum, Heat, and Mass Transfer (2nd ed.), McGraw-Hill, New York, 1984.

Siaghy, E. M., et al "Consequences of Static and Pulsatile on Transmembrane Exchanges During Vitro Microdialysis: Implication for Studies in Cardiac Physiology," Med Biol Eng Comput, vol. 37, 1999, pp. 196-201.

Utsunomiya, T., et al, "Effect of Direct Pulsatile Peritoneal Dialysis on Peritoneal Permeability and Lymphatic Absorption in the Rat," Nippon Jinzo Gakkai Shi, vol. 37, 1995, pp. 24-28.

Jaffrin, M. Y., et al, "Rationale of Filtration Enhancement in Membrane Plasmapheresis by Pulsatile Blood Flow," Life Support Systems, vol. 5, 1987, pp. 267-271.

Kobayashi, E., "A Study of Inorganic Ion Exchangers VII; The Synthesis of gammaNH4ZrH(PO4)2 And Ion-Exchange Properties of gamma-NH4Zr(HPO4)2.2H2O," Bull Chem Soc Jpn, vol. 56, 1983, pp. 3756-3760.

Suri, R, et al, "Adequacy of Quotidian Hemodialysis," Am J Kidney Dis, vol. 42 Suppl. 1, 2003, pp. S42-S48.

Gotch, F. A., "The Current Place of Urea Kinetic Modelling with Respect to Different Dialysis Modalities," Nephrol Dial Transplant, vol. 13 Suppl. 6, 1998, pp. 10-14.

Gotch, F. A., et al, "Effective Diffusion Volume Flow Rates (Qe) for Urea, Creatinine, And Inorganic Phosphorous (Qeu, Qecr, QeiP) During Hemodialysis," Semin Dial, vol. 16, 2003, pp. 474-476.

Roberts, Martin. "Wearable Artificial Kidneys for Continuous Dialysis," ASAIO Journal, 1993, pp. 19-23.

Murisasco, A, et al. "Continuous Arterio-venous Hemofiltration in a Wearable Device to Treat End-Stage Renal Disease," Trans Am Soc Artif Intern Organs, vol. XXXII, 1986, p. 567.

Murisasco, A, et al. "A Continuous Hemofiltration System Using Sorbents for Hemofiltrate Regeneration," Clinical Nephrology, vol. 26, Supp. No. 1-1986, pp. S53-S57.

Lande, Arnold J., et al. "In Search of a 24 Hours Per Day Artificial Kidney," Journal of Dialysis, 1(8), 1977, pp. 805-823.

Shettigar, "Portable Artificial Kidney With Advantages of Hemodialysis, Hemofiltration, and Hemoperfusion," Artificial Organs, 1982, vol. 1981, No. 5; pp. 645-649.

Henderson, "Continuous Low Flow Hemofiltration With Sorbent Regeneration of Ultrafiltrate," Transactions-American Society for Artificial Internal Organs, 1978, vol. 24; pp. 178-184.

* cited by examiner

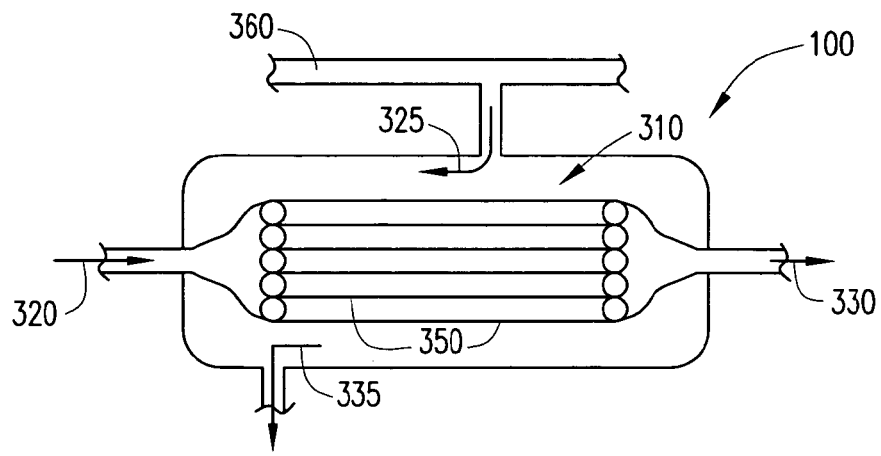
FIG. 5
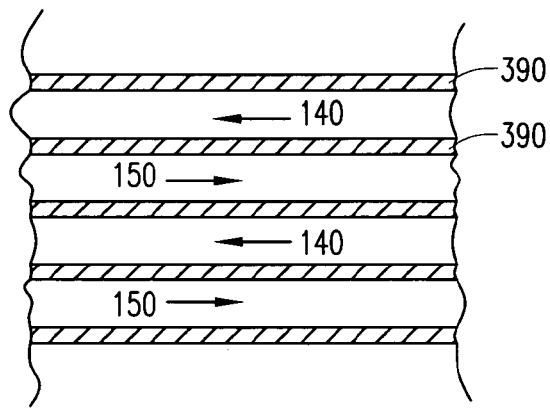
FIG. 6
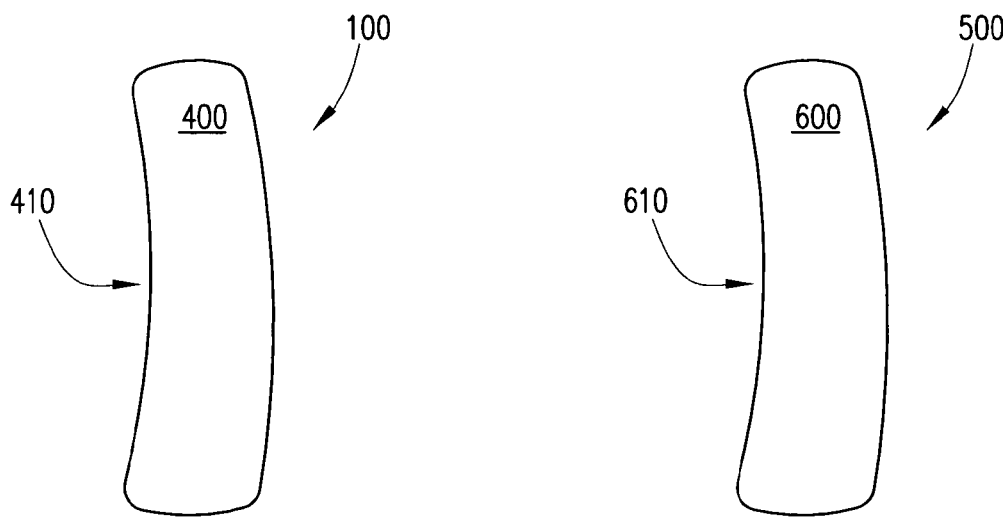
FIG. 7
FIG. 11

WEARABLE CONTINUOUS RENAL REPLACEMENT THERAPY DEVICE

CROSS REFERENCE TO RELATED APPLICATIONS

This application is a Continuation of U.S. patent application Ser. No. 10/940,862, filed Sep. 14, 2004, and entitled WEARABLE CONTINUOUS RENAL REPLACEMENT THERAPY DEVICE, which is a Continuation-in-Part of U.S. patent application Ser. No. 10/085,349, filed Nov. 16, 2001. The specifications of which are incorporated herein in their entirety by reference.

TECHNICAL FIELD

The present invention is directed to dialysis systems, and more particularly to a dialysis system that may be continuously worn by a patient.

BACKGROUND OF THE INVENTION

Hemodialysis is a process by which microscopic toxins are removed from the blood using a filtering membrane such as a dialyzer. Typically, hemodialysis is administered in intermittent three to four hours sessions, which take place two or three times per week. However, there exists a growing body of research that prefers daily dialysis since increased dialysis time improves outcomes both in terms of quality of life and longevity. However, the implementation of daily dialysis is almost impossible due to manpower and cost constraints. Furthermore, continuous renal replacement therapy (CRRT) over intermittent dialysis since far more toxins can be removed from the blood using CRRT seven days a week, twenty-four hours a day. Some advantages of CRRT include an expected decrease rate of morbidity and mortality, a decrease in the amount of medications required, a decrease in fluid intake and dietary restrictions, and numerous improvements in the quality of life of the ESRD patients Existing CRRT machines are large, heavy machines adapted to provide around the clock dialysis, hemofiltration or a combination of both to individual patients. The existing CRRT machines are cumbersome and must be hooked to electrical outlets and several feet of tubing. In addition, these machines require a continuous supply of gallons of fresh water to create dialysate fluid. Further, a patient must remain connected to the existing heavy and cumbersome CRRT machine for many hours, limiting his or her ability to perform normal every day activities.

An additional problem with existing dialysis machines, is that frequent reconnection to the machine requires accessing blood flow by puncturing an arteriovenous shunt. These shunts only last for limited periods of time and are subject to infection, clotting and other complications that result in numerous hospitalizations and repeated surgical interventions.

Unsuccessful attempts have been made to create a wearable dialysis device. Because of the bulky nature of typical dialyzers and associated sorbent devices, the concept of a wearable dialysis device has yet to become a reality for dialysis patients. In view of the above disadvantages, there continues to be a substantial need for a portable, wearable CRRT device, which can be used substantially continually, 24 hours a day, seven days a week.

SUMMARY OF THE INVENTION

One embodiment of the present invention involves a wearable CRRT device adapted to be worn on a portion of the body of a patient, including at least one or a plurality of dialyzers connected in series or parallel that utilize dialysate to remove impurities from the blood of the patient and at least one sorbent device for regenerating the spent dialysate.

Another embodiment of the present invention involves a wearable CRRT device adapted to be worn on a portion of the body of a patient, including at least one or a plurality of dialyzers, which comprise a plurality of cylindrical hollow fibers; wherein the patient's blood is circulated within the hollow fibers in a first direction and wherein the dialysate is circulated around the exterior walls of the hollow fibers in a second, opposite direction; wherein the exterior walls of the hollow fibers are semiporous so that impurities can be moved from the blood and into the dialysate.

An additional embodiment of the present invention involves a CRRT device adapted to be worn on a portion of the body of a patient, including a plurality of dialyzers, which comprise a plurality of parallel sheets of semiporous material, wherein the patient's blood is circulated on one side of the parallel sheets in a first direction and wherein the dialysate is circulated on the other side of the parallel sheets in a second, opposite direction.

A further embodiment of the present invention involves a CRRT device adapted to be worn on a portion of the body of a patient, including a plurality of dialyzers; wherein the number of dialyzers in the plurality of dialyzers may be varied to reflect different dialysis prescriptions; wherein at least one or each of the plurality of dialyzers has a flexible or semi-rigid casing adapted to conform to the body contour of the patient.

Yet another embodiment of the present invention involves a CRRT device adapted to be worn on a portion of the body of a patient, including a plurality of dialyzers having a blood inlet tube with a side port for the infusion of additives; wherein the additives are pumped into the blood from a plurality of additive reservoirs and the rate of infusion of each additive is controlled electronically.

Another embodiment of the present invention involves a CRRT device adapted to be worn on a portion of the body of a patient, including at least one dialyzer that utilizes dialysate to remove impurities from the blood of the patient and a plurality of sorbent devices connected in series for regenerating the dialysate.

A further embodiment of the present invention involves a CRRT device adapted to be worn on a portion of the body of a patient, including a plurality of sorbent devices; wherein each of the sorbent devices has a flexible casing adapted to conform to the body contour of the patient.

An additional embodiment of the present invention involves a CRRT device adapted to be worn on a portion of the body of a patient, including a series of sorbent devices; wherein the series of sorbent devices is a series of replaceable cartridges, which may include activated charcoal, urease, zirconium phosphate, hydrous zirconium oxide and/or activated carbon.

A further embodiment of the present invention involves a CRRT device adapted to be worn on a portion of the body of a patient and include a plurality of dialyzers connected in parallel.

Yet another embodiment of the present invention involves a CRRT device adapted to be worn on a portion of the body of a patient, include a plurality of sorbent devices connected in parallel.

Further applicability of embodiments of the present invention will become apparent from a review of the detailed description and accompanying drawings. It should be understood that the description and examples, while indicating preferred embodiments of the present invention, are not intended to limit the scope of the invention, and various changes and modifications within the spirit and scope of the invention will become apparent to those skilled in the art.

BRIEF DESCRIPTION OF THE DRAWINGS

The present invention will become more fully understood from the detailed description given below, together with the accompanying drawings, which are given by way of illustration only, and are not to be construed as limiting the scope of the present invention. In the drawings:

FIG. 5 is a cross-sectional view of a first embodiment of a dialyzer of the wearable CRRT device according to the present invention.

FIG. 6 is a cross-sectional view of a second embodiment of a dialyzer of the wearable CRRT device according to the present invention.

FIG. 7 is a top view of a casing of a dialyzer of the wearable CRRT device according to the present invention.

FIG. 11 is a top view of a casing of a sorbent device of the wearable CRRT device according to the present invention.

DETAILED DESCRIPTION

Figure 1:
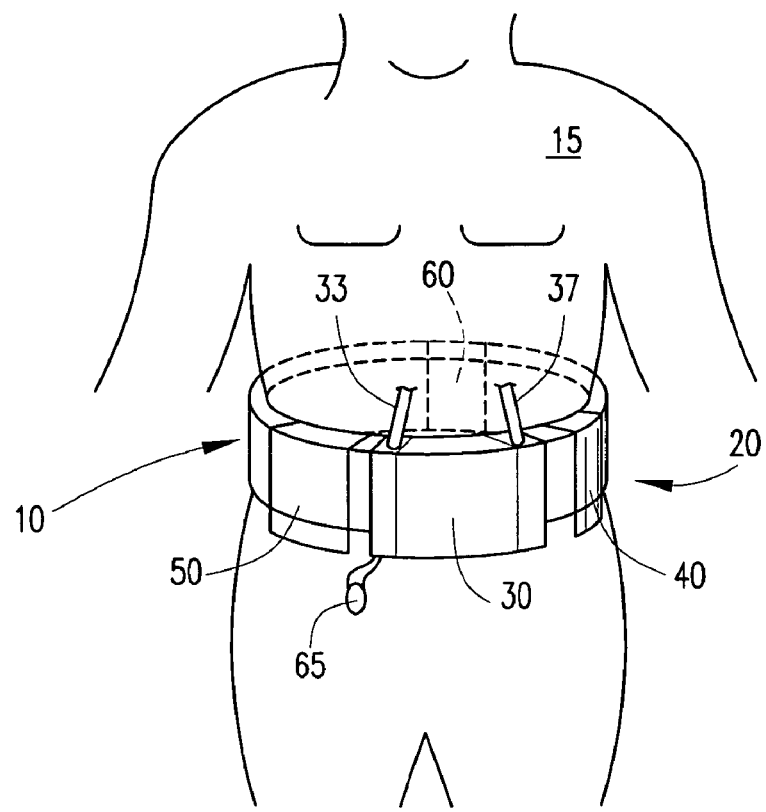
FIG. 1 is a perspective view of the wearable CRRT device worn around the waist of a dialysis patient according to the present invention.
Figure 2:
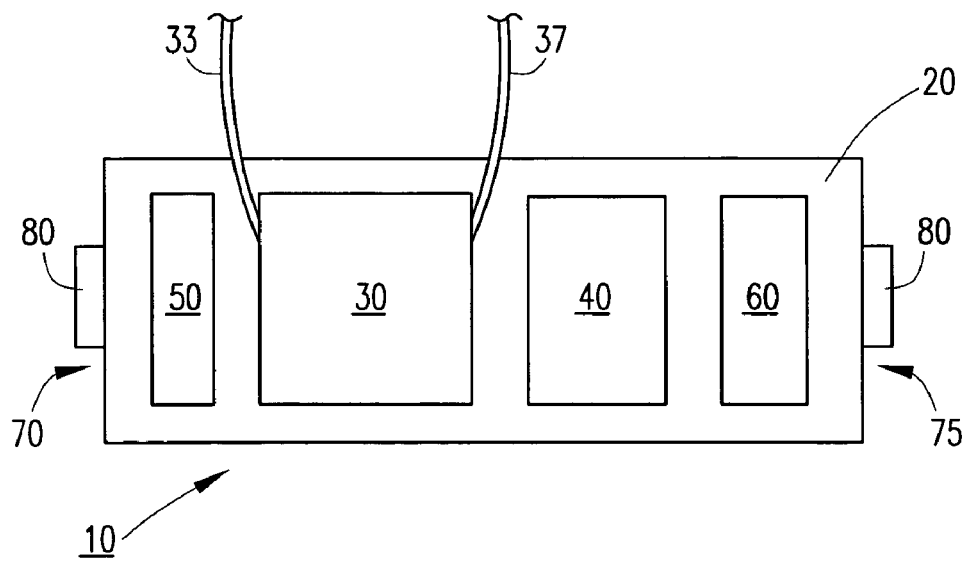
FIG. 2 is a front view of the wearable CRRT device of FIG. 1 after being detached from the dialysis patient.

Referring to FIGS. 1 and 2, a continuous renal replacement therapy (CRRT) device 10 is adapted to be worn about a portion of the body of a dialysis patient 15. The CRRT device 10 includes a belt 20 that is divided into a number of sections comprising: a dialyzer section 30 including a blood inlet tube 33 leading from a blood vessel and a blood outlet tube leading to a blood vessel; a sorbent section 40; an additive pump section 50; and an electronic control section 60, which includes a microprocessor and batteries to power device 10.

As best seen in FIG. 2, the belt 20 includes a pair of end portions 70, 75, which are secured together by a conventional belt fastener 80 such as a buckle, snaps, buttons or hook and loop fasteners. Although the CRRT device 10 depicted in FIG. 1 is worn about the waist of the patient 15, it should be understood to those of ordinary skill in the art that the device 10 may, alternatively, be worn about other portions of the patient's body, such as over a shoulder of the patient, for example.

Figure 3:
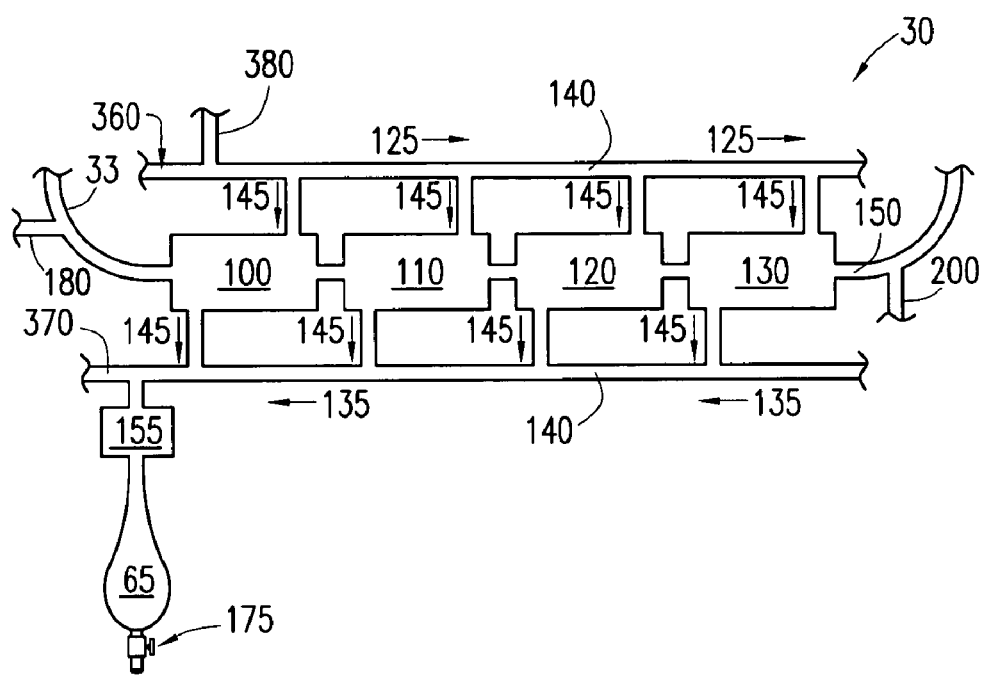
FIG. 3 is a perspective view of the dialyzer section of the wearable CRRT device according to the present invention.

Referring to FIG. 3, the dialyzer section 30 of the belt 20 includes a plurality of miniaturized dialyzers 100, 110, 120, 130 that utilize dialysate fluid 140 to remove impurities from the blood 150 of the patient 15. The number of dialyzers 100, 110, 120, 130 in the plurality of dialyzers 100, 110, 120, 130 may be varied to reflect different dialysis prescriptions. As best seen in FIG. 3, the plurality of dialyzers 100, 110, 120, 130 are connected in series, whereby a conventional pump forces the patient's blood 150 through a blood inlet tube 33, through the dialyzers 100, 110, 120, 130 and into blood outlet tube 37. It should be understood to those of ordinary skill in the art that the dialyzers 100, 110, 120, 130 could also be connected in parallel without departing from the scope of the invention.

During dialysis, the dialysate is pumped in the opposite direction of the blood flow using a conventional pump (not shown) as indicated by arrows 125, 135, 145. Spent dialysate 140 flows toward sorbent section 40 through spent dialysate tube 370. Excess fluid is removed from the spent dialysate 140 through a volumetric 155 and into a waste receiver 65, which is to be periodically emptied by the patient via tap 175. A microprocessor in the electronic section 60 determines the rate and amount of fluid removal through volumetric pump 155.

Figure 4:
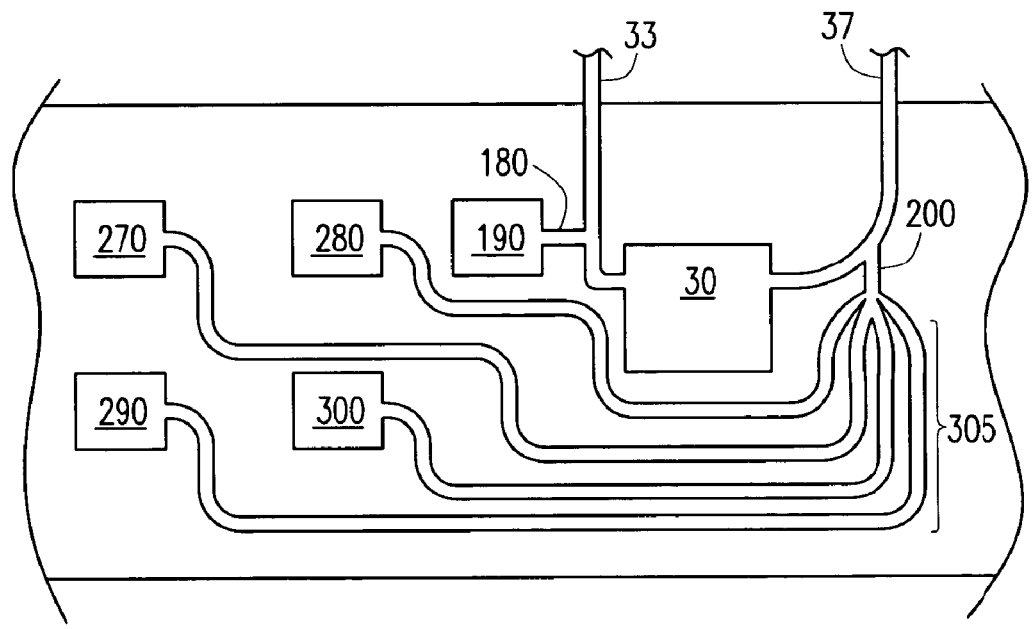
FIG. 4 is a perspective view of the additive pump and dialyzer sections of the wearable CRRT device according to the present invention.

With further reference to FIG. 3, the blood inlet tube 33 includes a side port 180 through which anticoagulant is pumped into the blood by anticoagulant pump 190. Typical anticoagulants are infused into the blood 150 include, but are not limited to, heparin, prostacyclin, low molecular weight heparin, hirudin and sodium citrate. As best seen in FIG. 4, the blood outlet tube 37 includes a side port 200 for the infusion of additives, which are forced into the blood 150 from a plurality of additive pumps 270, 280, 290, 300. Piston, suction, piezo, micro, or very small roller pumps can be employed for this purpose. Such pumps may all be classified as micropumps. Each additive pump 270, 280, 290, 300 forces a controlled amount of respective additive into the blood 150, wherein the rate of infusion of each additive is controlled electronically by the microprocessor in the electronic control section 60. In a known manner, a physician can use the electronic control section 60 to set the rate of infusion for each additive to correspond to a predetermined dose for each additive. Since the additives cannot be mixed together prior to infusion in the blood 150, they have separate circuits 305. Typical additives include, but are not limited to, sodium citrate, calcium, potassium and sodium bicarbonate.

Referring to FIG. 5, in a first dialyzer embodiment, each dialyzer 100, 110, 120, 130 is a conventional dialyzer comprising a plurality of cylindrical hollow fibers 310 through which the blood 150 is circulated. As indicated by arrows 320, 330, the dialysate fluid 140 is circulated around exterior walls 350 of the hollow fibers 310 in a direction across the blood flow inside the hollow fibers 310 as indicated by arrows 325, 335. The exterior walls 350 of the hollow fibers 310 are semiporous so that impurities can be moved from the blood 150 and into the dialysate 140. Fresh dialysate 140 flows from the sorbent section 40 through a dialysate inlet tube 360 and into the series of dialyzers 100, 110, 120, 130. The spent dialysate 140 then flows out of the series of dialyzers 100, 110, 120, 130, through a spent dialysate outlet tube 370 and into the sorbent section 40. The dialysate inlet tube 360 includes a side port 380 (shown in FIG. 3) for the infusion of additives, which can be forced into the blood 150 via the aforementioned additive pumps 270, 280, 290, 300, whereby the rate of infusion is controlled electronically by the microprocessor in the electronic control section 60. Referring to FIG. 6, in second dialyzer embodiment, each dialyzer 100, 110, 120, 130 comprises a plurality of parallel sheets 390 of semiporous material, wherein the dialysate fluid 140 is circulated on one side of the parallel sheets 390 and the blood 150 circulates in the direction on the other side of the parallel sheets 390.

Referring to FIG. 7, each dialyzer 100, 110, 120, 130 is a miniature dialyzer having a flexible casing 400 adapted to conform to the body contour of the patient. In addition, the body-side wall 410 of each casing 400 is concave to further correspond to bodily curves of the user. The casing 400 can, be made of any suitable material having adequate flexibility for conformance to the portion of the body to which it is applied. Suitable materials include, but are not limited to, polyurethane and poly vinyl chloride.

Figure 8:
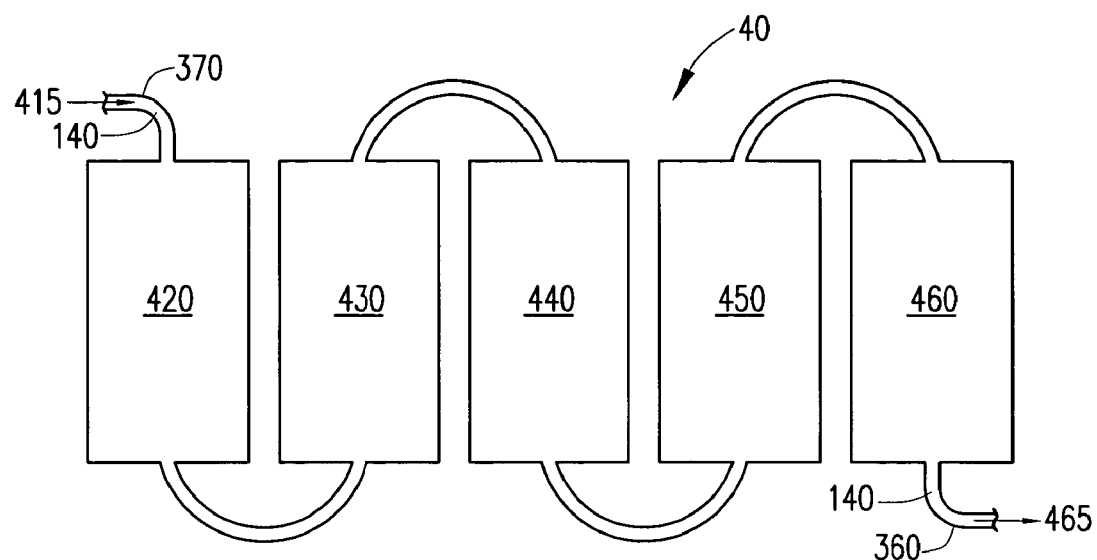
FIG. 8 is a perspective view of a first embodiment of the sorbent section of the wearable CRRT device according to the present invention.
Figure 9:
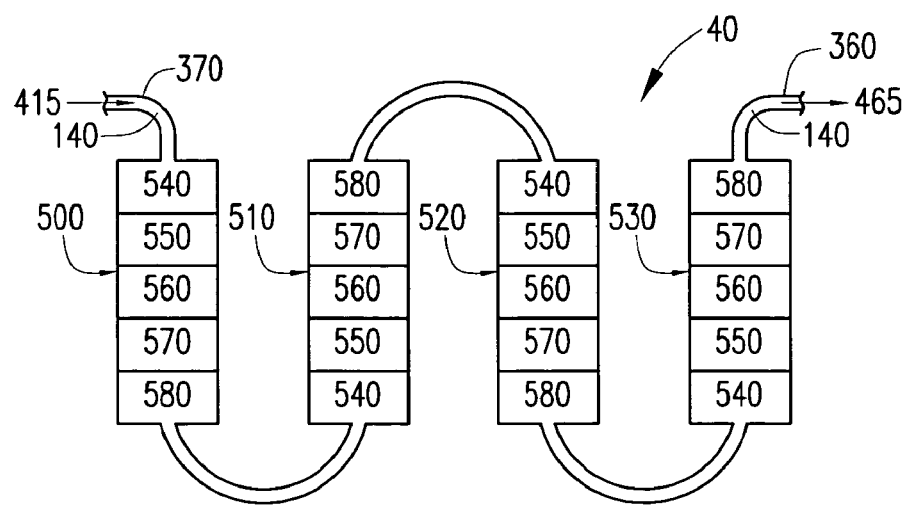
FIG. 9 is a perspective view of a second embodiment of the sorbent section of the wearable CRRT device according to the present invention.
Figure 10:
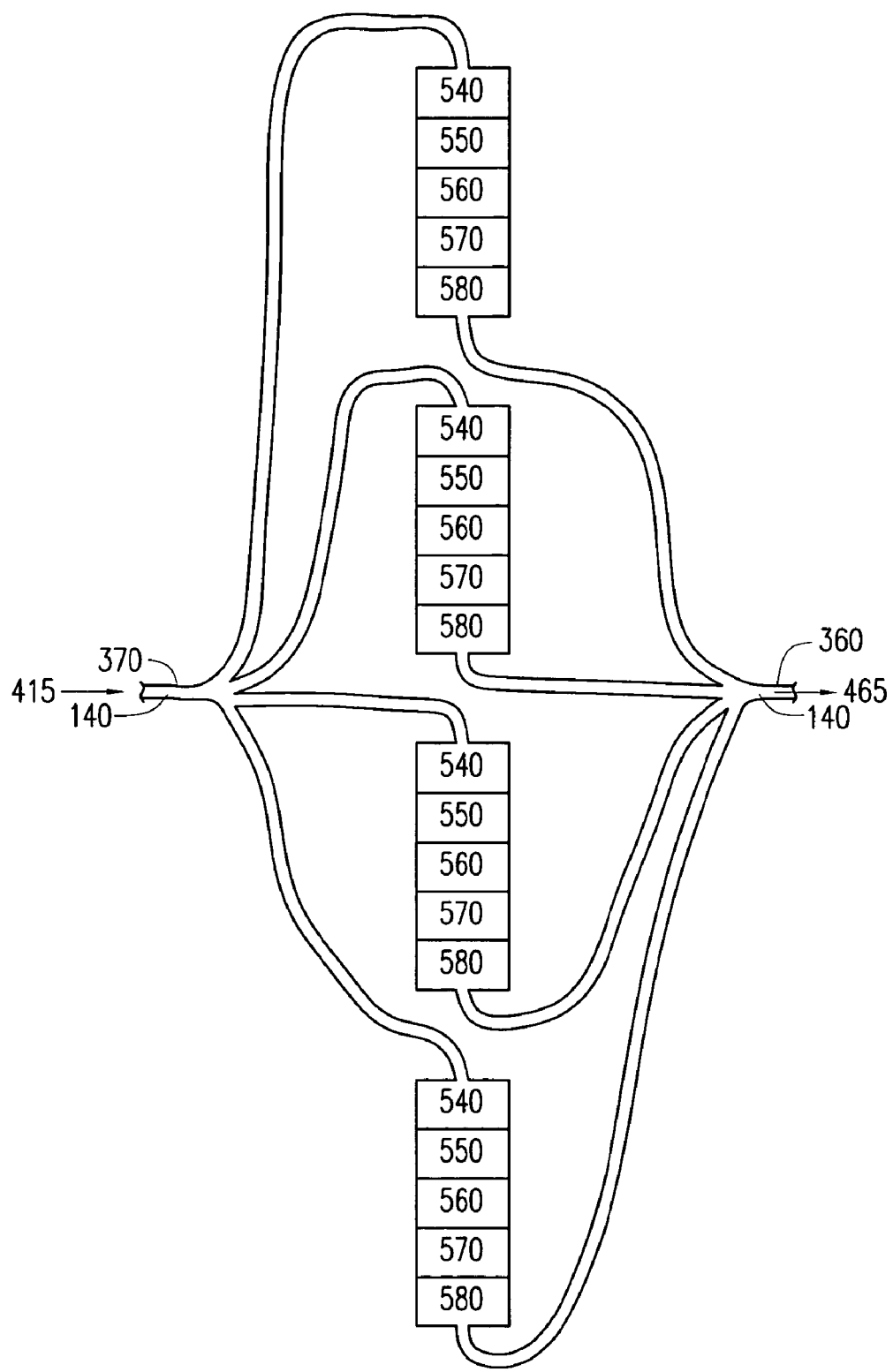
FIG. 10 is a perspective view of a variation of the second embodiment of the sorbent section of the wearable CRRT device according to the present invention.

Referring to FIG. 8-10, in the sorbent section 40, as indicated by arrow 415, spent dialysate 140 flows from the dialyzer section 30 through spent dialysate tube 370 and into a plurality of sorbent devices 420, 430, 440, 450, 460. As indicated by arrow 465, the regenerated dialysate 140 then flows through tube 360 and back into the dialyzer section 30. Preferably, the sorbent devices 420, 430, 440, 450, 460 comprise a series of sorbent cartridges 420, 430, 440, 450, 460 for regenerating the spent dialysate 140. By regenerating the dialysate with sorbent cartridges 420, 430, 440, 450, 460, the exemplary CRRT device 10 requires only a small fraction of the amount of dialysate of a single-pass hemodialysis device. Importantly, each sorbent cartridge 420, 430, 440, 450, 460 is a miniaturized sorbent cartridge 420, 430, 440, 450, 460 containing a distinct sorbent.

Referring to FIG. 8, in a first embodiment of the sorbent section 40, there are five sorbent cartridges 420, 430, 440, 450, 460 including an activated charcoal cartridge 420, a urease cartridge 430, a zirconium phosphate cartridge 440, a hydrous zirconium oxide cartridge 450 and an activated carbon cartridge 460. Those of ordinary skill in the art will recognize that these sorbents are similar to the sorbents employed by the commercially available Recirculating Dialysis (REDY) System. However, in the REDY System, the sorbents are layers of a single cartridge. By contrast, the sorbents of the present invention are each part of a distinct sorbent cartridge 420, 430, 440, 450, 460 such that each cartridge 420, 430, 440, 450, 460 may, conveniently, be replaced and disposed of independently of the other cartridges 420, 430, 440, 450, 460 if so desired. As one of ordinary skill in the art would understand, activated charcoal, urease, zirconium phosphate, hydrous zirconium oxide and activated carbon are not the only chemicals that could be used as sorbents in the present CRRT device 10. In fact, any number of additional or alternative sorbents could be employed without departing from the scope of the present invention.

Referring to FIGS. 9 and 10, in a second embodiment of the sorbent section 40, there are a plurality of sorbent cartridges 500, 510, 520, 530, wherein each cartridge 500, 510, 520, 530 includes a plurality of sorbent layers 540, 550, 560, 570, 580: an activated charcoal layer 540, a urease layer 550, a zirconium phosphate layer 560, a hydrous zirconium oxide layer 570 and an activated carbon layer 580. The cartridges 500, 510, 520, 530 may be in series as depicted in FIG. 9 or may be in parallel as depicted in FIG. 10. In this embodiment, the number of sorbent devices may be varied to correspond with different dialysis prescriptions.

Referring to FIG. 11, each cartridge 500, 510, 520, 530 is a miniature cartridge having a flexible or curved casing 600 adapted to conform to the body contour of the patient. In addition, the body-side wall 610 of each casing 600 is concave to further correspond to bodily curves. The casing 600 can be made of any suitable material having adequate flexibility for conformance to the portion of the body to which it is applied. Suitable materials include, but are not limited to, polyurethane and poly vinyl chloride.

Figure 12:
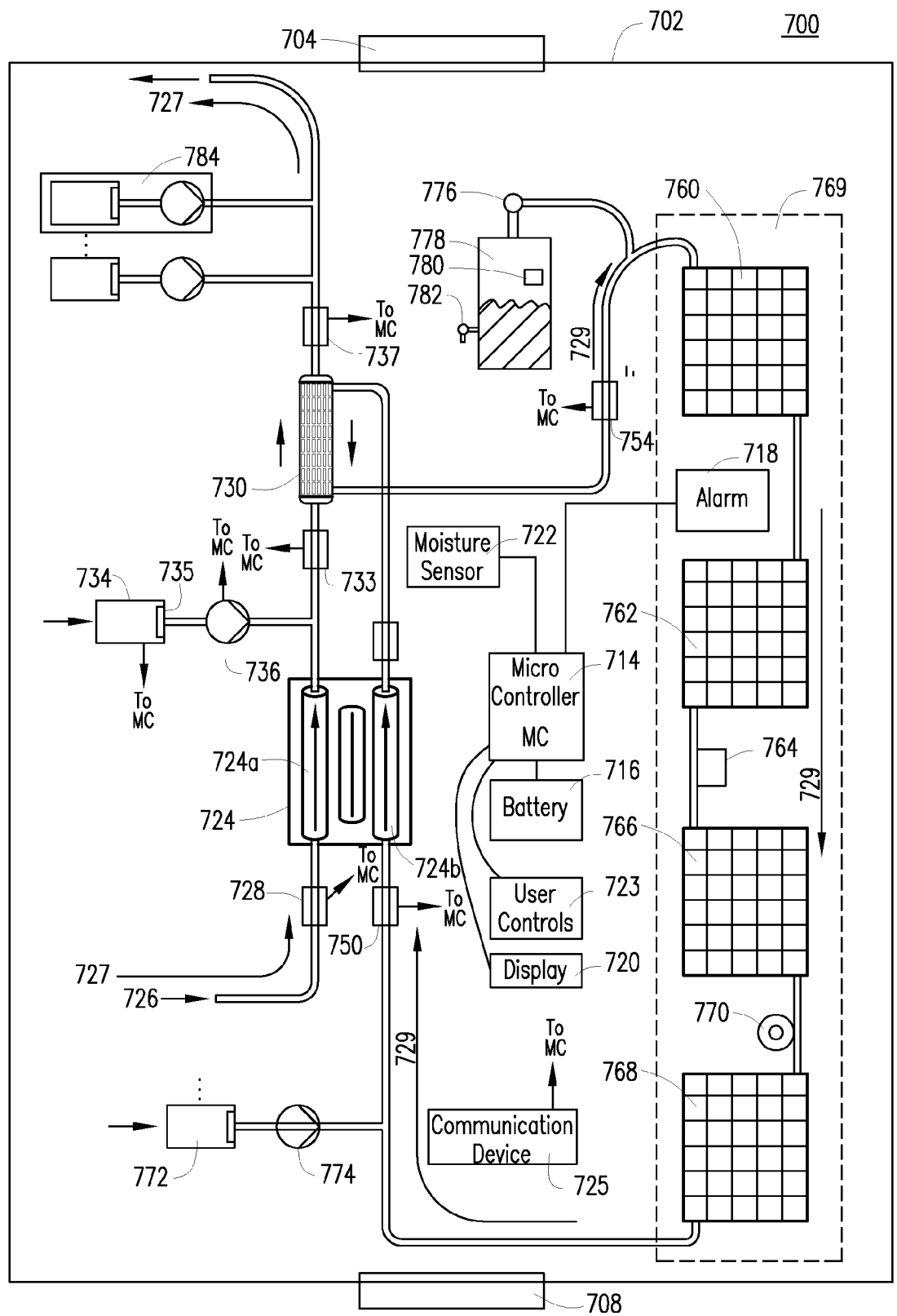
FIG. 12 is a diagram of an exemplary embodiment of the wearable CRRT device.
Figure 13A:
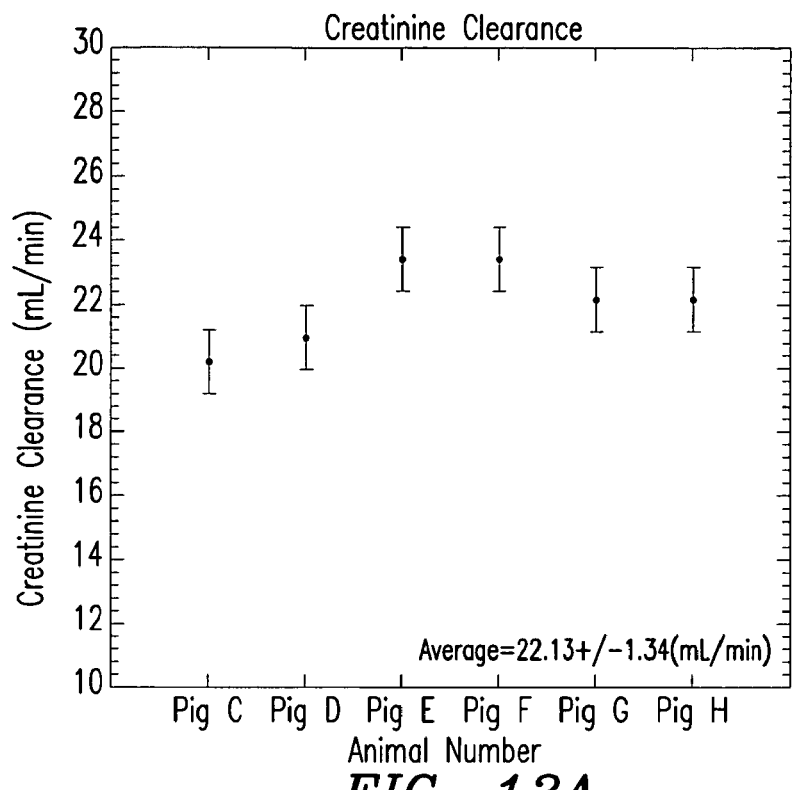
FIGS. 13A-13E are charts indicating experimental results using an embodiment of the wearable CRRT device.
Figure 13B:
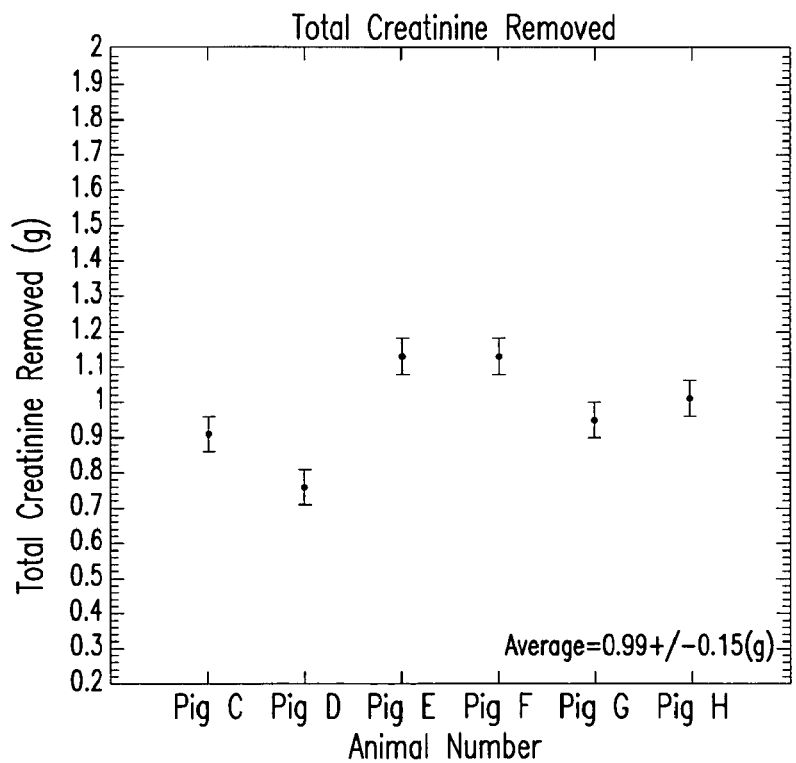
Figure 13C:
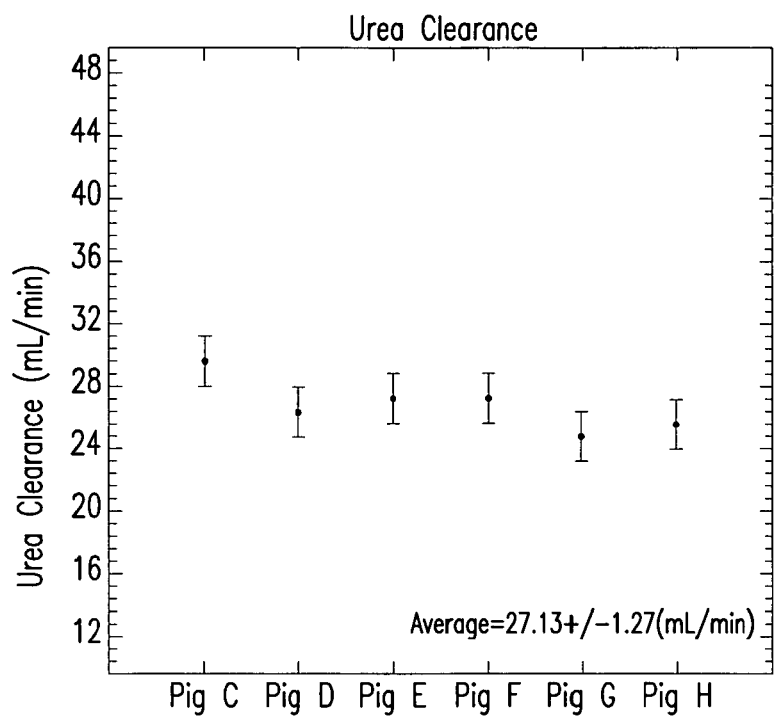
Figure 13D:
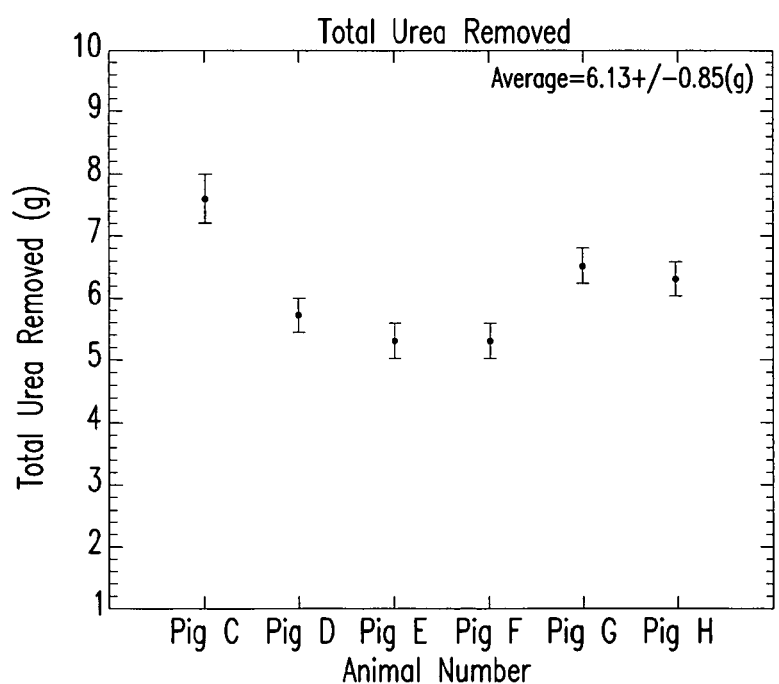
Figure 13E:
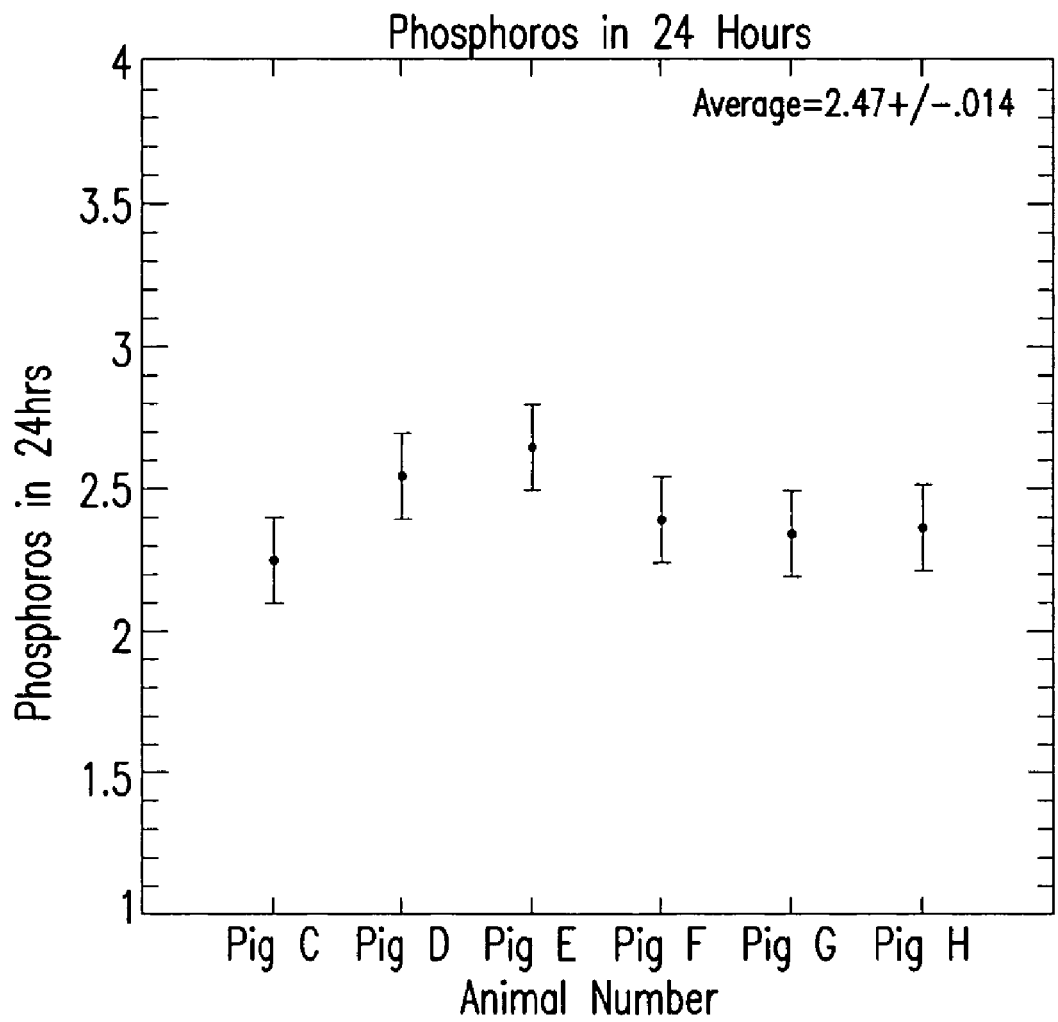

Referring to FIG. 12, another exemplary embodiment of a wearable CRRT device is depicted. The wearable CRRT device 700 is built into, or is part of, a patient wearable strap, belt or other wearable apparatus 702. The belt 702 may include a pair of endportions 704, 708 that are adapted to be secured together by a fastening means (not specifically shown). The endportion/fastening means 704, 708 could be any number of fastening devices suitable to secure the ends of the belt or strap together, but not limited to snaps, button, buckles, clips, laces, hook and loops, zippers, clasps, etc. An embodiment of a CRRT device may be envisioned to be the shape of an ammunition or military style supply belt, it could also be the shape of a waist-pack. An exemplary wearable CRRT device 700 is worn by a patient either over or under other clothing.

A microcontroller 714 is utilized to control and monitor various aspects of the wearable CRRT device 700. The microcontroller 714 is preferably a low or very low power microcontroller, but may be substantially any microcontroller adapted to operate in an exemplary wearable CRRT device 700. One of the many functions of the microcontroller 714 has is to monitor the battery 716. An exemplary CRRT device 700 will operate continuously for at least 5 to 10 hours using less than 10 continuous watts of power. And preferably less than 3 continuous watts of power. Embodiments of the invention weight less than 10 lbs and preferably less than 5 lbs when operating.

The battery 716 is removably installed in the wearable CRRT device 700. The battery 716 is rechargeable and may be recharged while remaining in the wearable CRRT device 700 via a charging device (not shown) or when disconnected from the wearable CRRT device 700. Preferably the battery 716 can store enough energy to power a wearable CRRT device 700 for at least five (5) or more hours of continuous uninterrupted device operation. The microcontroller, by itself, or via additional circuitry, monitors the charge status of the battery 716. If the microcontroller 714 determines that the battery 716 is low on charge or has less than an estimated predetermined amount of operating time left (e.g., one hour left), the microcontroller 714 may trigger an alarm condition via alarm circuit 718. Alarm circuit 718 may provide any combination of an audio, visual, or physical alarm. The physical alarm signal may include vibrations or small tingle-style shocks to the patient. An alarm condition or warning may be displayed on the display 720 using liquid crystal, light emitting diode or other low power display technology. An alarm condition may also shut down all or predetermined parts of an exemplary wearable CRRT device 700.

A moisture sensor 722 is also in electrical communication with the microcontroller 714. The moisture sensor 722 is used to detect high humidity, condensation, or liquid present inside the packaging or covering over (not specifically shown) the wearable CRRT device 700. The packaging or covering over an exemplary CRRT device 700 may be a plastic, cloth, rubberized, poly-product, or other suitable material. The covering may cover a portion of the wearable CRRT device 700 and allow access to various parts of the device such as the display 720 and user/doctor controls 723.

High humidity, condensation or the presence of liquid inside a wearable CRRT device 700 may be indicative of patient blood leakage, dialysate leakage or other fluid leakage. Upon sensing moisture, the moisture sensor 722 provides a signal to the microcontroller 714 and an alarm is triggered via the alarm circuit 718. Furthermore, the pump 724 may be turned off by the microcontroller 714 to help minimize further blood, dialysate or other fluid loss. The microcontroller may shut down the micropumps (to be discussed later) also. The microcontroller 714 may also prompt an onboard communication device 725 to contact medical help or another entity for medical assistance. The communication device may comprise a paging wireless phone or other mobile communication circuitry. The communication device 725 may also be able to provide the geographic location of the exemplary wearable CRRT device 700.

The pump 724 is an electric pump. The pump 724 may be two pumps 724a and 724b. The two pumps 724a and 724b may each operate off the same or separate electric motors. The pumps 724a and b are powered by the rechargeable battery 716. Furthermore, the microcontroller 714 can be used to adjust various pumping variables. Potential adjustable pumping variables include, but are not limited to, adjusting the pump stroke, volume-per-stroke, speed, torque, pumping rate (i.e., number of pump cycles per minute), pump pressure, pump pressure differential between the input and output of the pump, and pump pause and cycle times.

An exemplary wearable CRRT device 700 has two fluid circuits: a blood circuit 727 and a dialysate circuit 729. A dual channel pulsatile pump 724 may be used in an exemplary embodiment. A pulsatile pump, in general, has a rubberized cartridge for each channel. A cartridge has an input valve at an input side of the cartridge and an output valve at an output end of the cartridge. FIG. 12 depicts a single direction, dual pulsatile pump 724. A dual direction, dual pulsatile pump may also be utilized. A dual direction channel pump is preferred in order to decrease bending of the tubing used in the fluid circuits.

The motor and transmission within the pulsatile pump presses the rubberized, tubular portion of the cartridge. The pressing of the cartridge squeezes and evacuates the contents of the cartridge out of the output valve. As the pump motor spins and causes the mechanics of the pump to release pressure from the rubberized portion of the cartridge, the output valve closes and the input valve opens to allow fluid (blood or dialysate) to enter the cartridge so that the fluid can be squeezed out the output valve in the next pump cycle. The input and output valves are one-way valves allowing fluid flow in a single direction through the cartridge. Other configurations of a pulsatile pump are also available. An exemplary pump 724a, 724b provides a blood flow rate of between about 15 to 100 ml/min (pulsatile). The approximate dimensions of an exemplary dual-pulsatile pump 724 is 9.7×7.1×4.6 cm with a weight of less than 400 grams. An exemplary pulsatile pump uses less than 10 watts of energy and may provide a low battery power and a pump occlusion alarm signal to the microcontroller 714. A lower power pulsatile pump using 5 or less watts may also be used.

The pulsatile pump can be tuned such that the pulses, or cycles, of the two pulse chambers are in phase, 180° out of phase or any predetermined number of degrees out of phase in order to utilize the pulses of the pump to aid in maximizing the dialysis process occurring in the dialyzer 730. The opposite directional flows of blood and dialysate through the dialysate may become more efficient at different phase settings of the pumps 724a and b.

Other types of pumps 724 can be successfully used or incorporated into embodiments of the wearable ultrafiltration device. Two separate pumps may also be used. Such other types of pumps include, but are not limited to, a shuttle pump, a piston pump, a roller pump, a centrifuge pump, a piezo electric pump, or other conventional pumps. Whatever pump is utilized, the pump(s) 724 should have a manually or electrically adjustable flow rate ranging somewhere between 20 ml/min and 120 ml/min.

The microcontroller 714 may display pump status or other pump related information on the display 720. User controls 723, being buttons, switches, slide controls, knobs, connectors, or infrared receiver (not specifically shown) may be used to enable a patient, physical, nurse, technician or computer based device to adjust various settings and controls on an exemplary ultrafiltration device 700. Furthermore, the communication device 725 may be utilized to receive control settings and send information via paging or other telecom communication channels. For example, the adjustments to the pump 724 pump rate, torque, valve opening size, output pressure, flow rate, rpm, and on/off may all be monitored or controlled via the user interface 723 or the communication device 725.

Discussing the exemplary blood circuit 727 first, blood from the patient enters the blood circuit 727 via the blood inlet tube 726. An input blood pressure transducer 728 measures the input blood pressure and provides an input blood pressure signal to the microcontroller 714 (connection to microcontroller not specifically shown). The input blood pressure may be an average pressure of the blood prior to entering the pump 724a. The blood is then pumped through the pump 724a.

After the blood passes through the main pump 724a, it continues in the blood circuit 727 via the blood inlet tube 726. An input blood pressure transducer 728 measures the input blood pressure and provides an input blood pressure signal to the microcontroller 714 (connection to microcontroller not specifically shown). The input blood pressure may be an average pressure of the blood prior to entering the pump 724a. The blood is then pumped through the pump 724a.

After the blood passes through the main pump 724a, it continues in the blood circuit 727. A reservoir 734 containing a blood thinner or anticoagulant such as heparin or another acceptable anticoagulant additive is connected to the blood circuit via a micropump 736. The micropump 736 provides the fluid contents of the reservoir 734, in a measured continuous or non-continuous manner, to the blood circuit 727 prior to the dialyzer 730. (It is possible to connect the reservoir 734/pump 736 combination to the blood circuit before the pump 724a.) The micropump 736 is a type of pump that can pump microscopic or miniscule amounts of fluid each minute. A micropump, in general, may pump fluid at a rate ranging from 1 to 400 ml/hr (milliliters per hour). A micropump requires from about 1 to 500 milliwatts to operate. There are, at present, various pumps that can be considered micropumps including, but not limited to, a piezoelectric pump, a solenoid pump, a micro-piston pump, a peristaltic pump, a nanotechnology related pump, microtechnology/micromachined pump, syringe style pump, roller pump, centrifuge style pump, or diaphragm style pump.

The blood thinner and/or anticoagulant may be mixed or combined with the blood in the blood circuit at any point between the inlet of blood inlet tube 726 and the blood input side of the dialyzer 730.

The reservoir 734 may have a fluid level sensor 735 or other type of sensor to sense the amount of fluid available in the reservoir 734. The sensor 735 provides a signal to the microcontroller 714 indicating an amount of fluid in the reservoir 734. The microcontroller 714 sends an alarm signal to the alarm circuit 718 if the fluid level or fluid amount in the reservoir 734 is below a first predetermined amount or volume. The microcontroller 714 may also turn the ultrafiltration device 700 off if the fluid level in reservoir 734 is at the first predetermined level or below the first predetermined level and at a second predetermined level.

The combination of the reservoir 734 and the micropump 736 infuse the blood thinner or anticoagulant into the blood flowing in the blood circuit 727. Again, the thinner or anticoagulant is infused into the blood prior to the dialyzer (or blood filter) 730 (in some embodiments prior to the blood pump 724*a*) in order to help minimize the potential of blood clots in the blood filter 730 and perhaps in the blood pump 724*a*.

A second pressure transducer 733 senses the pressure in the blood circuit after the blood pump 724*a*, but before the dialyzer 730. The pressure reading is supplied to the microcontroller (MC) 714 which monitors such readings.

A dialyzer 730, shown as a single dialyzer, can be a single or multiple dialyzer as discussed earlier. The dialyzer(s) may take the form of a cartridge that can be "clicked" or inserted into and out of the blood/dialysate circuits by a doctor, nurse or technician. The dialyzer may comprise from 0.2 to 1 sq. meters of dialyzing surface area. During dialysis the blood circuit 727 flows in the opposite direction as the dialysate circuit 729 in order to help maximize the dialysis process. Furthermore, the pulsing of the pumps 724*a* and *b* may, either in phase or out of phase, also aid in maximizing the dialysis processes.

The blood, after being dialyzed in the dialyzer 730, exits the dialyzer 730 and flows through a third pressure transducer 737. The third pressure transducer 737 provides a pressure signal to the microcontroller. The combination of the first, second and third transducers provide differential pressure measurements that are analyzed by the microcontroller 714. For example, if the pressure differential across the dialyzer 730 is too high it may mean, among other things, that the dialyzer 730 has a clot in it or is being operated at too high a blood flow. As a result, an alarm situation can be initiated or the blood pump 724*a* pumping rate or torque can be adjusted via microprocessor control. If the pressure at a transducer drops below a predetermined pressure it may be an indication of a fluid leak or that air is in the blood circuit 727. The microcontroller 714 may shut down all or predetermine parts of the wearable CRRT device 700 in response to pressure measured below a predetermined level.

The blood returns to the patient via the blood outlet tube 740. As shown in FIG. 4, a sideport 200 can be incorporated so that additional electrolytes, drugs, blood additives, vitamins or other fluids can be added to the blood in the blood circuit 727 via a reservoir/micropump combination prior to the blood being returned to the patient via the blood outlet tube 740.

Referring still to FIG. 12, the exemplary dialysate circuit will now be discussed. A fourth pressure transducer 750 measures the dialysate pressure at the input side of the dialysate pump 724*b* and provides the pressure reading to the microcontroller 714. The dialysate pump 724*b*, like the blood pump 724*a* is preferably part of a dual pump device 724 described above, but may be a separate pump device.

Cleaned, fresh dialysate from the sorbent filters 769 flows in the dialysate circuit 729 through the dialysate pump 724*b*. The dialysate pump 724*b* can pump dialysate at a flow rate ranging from near zero to 150 ml/min. The exemplary normal operating flow rate of the dialysate pump is between 40 and 100 ml/min.

Embodiments of the wearable CRRT device 700 are designed to operate using less than one liter of dialysate. Embodiments preferably only require 300 ml to 400 ml in the closed dialysate fluid circuit 729 to operate. An embodiment designed for a young adult or child may operate with about 100 to about 300 ml of dialysate. The combination of dialysate and filters 769 allow an embodiment to circulate dialysate for at least 24 hours before a filter requires replacement. Furthermore, because less than a liter of dialysate is all that is needed in the closed dialysate circuit 729, sterile or ultra-pure dialysate can be economically used in exemplary embodiments of the wearable CRRT device 700.

In normal or large dialysis machines it is common to use about 90 liters of dialysate per patient per run. Generally, due to of the amount of water required to create the dialysate, filtered water, rather than ultra-pure water, is used. Filtered water is much less expensive than ultra-pure or sterile water. Filtered water that is used in dialysis machines is allowed to have some bacteria in it. The bacteria is larger than the size of the pores in the membranes used in the dialyzer 730. Since the bacteria is larger than the pore size, the bacteria cannot cross the membrane and get into the blood.

Conversely, medical research has provided some results that are uncomfortable with the use of non-sterile dialysate (dialysate containing filtered water, bacteria, toxins, or micro organisms). The micro organisms and bacteria create waste products, toxins or poisons in the dialysate. The waste products from the bacteria can cross the dialyzer pores and get into the patient's blood while the actual bacteria cannot. Such toxins are referred to, in some cases, as endotoxins. The endotoxins that pass from the dialysate to the blood can have a negative effect on the patient's health. The endotoxins can make the patient sick.

Since exemplary embodiments of the wearable CRRT device 700 require less than one liter of dialysate it is economically feasible to use ultra-pure or sterile water when making the dialysate.

The dialysate exits the dialysate pump 724*b*, passes by another pressure transducer 752, which measures the dialysate pressure on the input side of dialyzer 730. The dialysate circuit 729 moves the dialysate into the dialyzer 730 such that the dialysate preferably moves in a direction opposite to the flow of blood through the dialyzer. While the dialysate is in the dialyzer to the dialysate 730, waste products and toxins in the blood pass through the membranes of the dialyzer to the dialysate thereby cleaning the patient's blood.

The dialysate exits the dialyzer 730 and flows through another pressure transducer 754. The pressure transducer 754 on the output side of the dialyzer 730 sends a signal to the microcontroller 714 indicating the pressure of the dialysate. The pressure may help indicate a clogged dialyzer, a leak or other emergency condition.

The dialysate circuit 729 takes the used, toxin or contaminant containing, dialysate to the first of a series of dialysate filters 769. The filters may filter or react with predetermined substances in the dialysate in order to recycle the dialysate for continued use in the dialysate circuit.

In an exemplary embodiment, the first filter 760 contains urease. The urease filters the used dialysate and further functions to break down urea that was removed from the blood in the dialyzer 730. When urease breaks down urea at least two unwanted bi-products are created. Generally, the two bi-products are ammonium (ammonia) and carbon dioxide.

The dialysate with the ammonia and carbon dioxide exit the first filter 760. The urea is substantially removed from the dialysate, but the ammonia and carbon dioxide need to be removed from the dialysate also. The dialysate, ammonia, and carbon dioxide enter the second filter 762. The second filter 762 contains a compound containing zirconium or zirconium phosphate (i.e., ZrPx). The zirconium in the second filter 762 captures the ammonia. It is understood by those having ordinary skill in the art of dialysis chemistry that various chemicals and derivations thereof can be utilized to achieve the same or similar results.

The zirconium filter, the second filter 762, will eventually become saturated with ammonia. The zirconium filter, when becoming saturated with ammonia, will become less efficient at removing ammonia from the dialysate. It is not advantageous to allow ammonia or ammonium to circulate through the dialysate circuit 729. Thus, in an exemplary wearable CRRT 700, a sensor 764 is placed in the dialysate circuit 729 to sense a presence of ammonia in the dialysate. The sensor 764 may be a ph sensor, an ammonia specific sensor, or a conductivity sensor. If an ammonia sensor is used it will sense whether a predetermined amount of ammonia is present in the dialysate. If a ph sensor is used, it would sense whether the ph of the dialysate has become a predetermined amount more alkaline than normal. When ammonia is present, the dialysate becomes more alkaline. It is noted that depending on the actual chemicals and absorbents used in the filters, the dialysate may become more acidic and as such a sensor would be used to sense the same. If a conductivity sensor is used, it will sense the conductivity changes of the dialysate.

The sensor 764 is in electrical communication with the microcontroller 714. If the signal read by or provided to the microcontroller 714 from the sensor 764 indicates that the second filter 762, the zirconium filter, is not adsorbing a majority or a predetermined amount of the ammonia in the dialysate, then an alarm condition is triggered by the microcontroller 714. The alarm condition would instruct the user that one or more filters (cartridges) need to be replaced. The alarm condition may also shut down predetermined functions of the wearable CRRT device 700. For example, one or more pumps 724 may be shut down or the pump rate of one or more pumps and micro pumps may be slowed. Slowing the pump rate may increase the amount of ammonia adsorbed by the zirconium based filters in the sorbent filter section 769.

The senor 764 that is used to sense the presence of ammonia in the dialysate is placed after the second filter 762 containing the zirconium phosphate. The sensor 764 may be placed after the third filter 766, that contains hydrous zirconium oxide or the fourth filter 768 which is a carbon filter. One or more sensors in the dialysate circuit will sense pressure, pH, ammonia, flow rate, temperature or other physical attributes. A sensor will provide a signal to the microcontroller indicating that the dialysate circuit needs maintenance.

The third exemplary filter 766 is a hydrous zirconium oxide (ZrOx) filter which may further remove contaminants and ammonia from the dialysate. A bubbler degasser, or valve device 770 may be part of a filter (i.e., 762, 766 or 768) or be a separate element, as shown, removes air, carbon dioxide and other gas bubbles from the dialysate. It is important that a limited amount of gas bubbles go through the dialyzer 730. As such a bubbler 770 (one or more) should be positioned prior to the pump 724b, but after the filter or filters that may cause gas bubbles to form in the dialysate.

The fourth exemplary filter 768 contains carbon and is used to further clean the dialysate of impurities via adsorption. The filters, as discussed previously, are preferably designed as filter cartridges. Each cartridge can be inserted and removed from the wearable CRRT device 700 by the patient, doctor, technician or nurse. Each filter cartridge 760, 762, 766, 768 may contain layers or combinations of chemicals or adsorbents. In fact, an exemplary embodiment may have a single cartridge filter containing layers of required substances to clean and refresh the dialysate after passing through the dialyzer 730. The filter cartridge(s) may each incorporate a bubbler device or the bubbler 770 may be a separate element in the dialysate circuit 729.

In an exemplary wearable CRRT device 700 the cartridge(s) may be replaced daily or every other day by the patient. Each filter cartridge should weigh less than half a pound dry. The combination of all the cartridges, dry, should weigh less than two pounds total. Each filter cartridge may have inner dimensions of about 4 cm×10 cm×10 cm or provide a volume of about 400 $cm^3$±100 $cm^3$ for each sorbent material. The total volume of all sorbent materials using in whatever quantity, combined, may be between about 400 $cm^3$±2,000 $cm^3$. In an exemplary embodiment a filter cartridge can be changed one a day or less often.

An additive reservoir 772 and micropump 774 may be connected to the dialysate circuit 729 after the filter cartridge(s) 769, but before the pump 724b. Although not specifically shown in FIG. 12 multiple reservoirs 772 and micropumps 774 can be connected to the dialysate circuit 729. The micropump(s) 774 may be any of the micropumps discussed above with respect to micropump 736. Here the micropump(s) 774 and reservoirs 772 may add chemicals and additives to freshen the dialysate and prolong its ability to act as a dialysate. An exemplary wearable CRRT device 700 may have as little as 300 ml to about one liter of dialysate in the dialysate circuit 729. It is important for the sorbent section 769 to be able to clean and freshen the dialysate continuously as it circulates about the dialysate circuit 729.

An exemplary wearable CRRT device 700 may also remove ultrafiltrate or fluids from the patient's blood. The patient's kidneys may not be functioning properly. After the dialysate leaves the dialyzer 730, and preferably before the dialysate enters the filter cartridge(s) 769, ultrafiltrate/dialysate, along with other contaminants and fluids obtained via the dialyzer 730, can be removed from the dialysate circuit 729 via a valve 776 and deposited in a fluid bladder 778. The fluid bladder 778 may hang below the wearable CRRT device 700 (not specifically shown) and be able to store from about 0.1 to 2 liters of fluid. A fullness sensor associated with the fluid bladder 778 is in electrical communication with the microcontroller 714 to enable an alarm condition when the fluid bladder 778 at a predetermined fullness.

The fluid bladder 778 may also be incorporated into the wearable CRRT device 700 as an empty cartridge that is filled via a micropump and valve combination 776. A fullness sensor 780 can aid the microcontroller to determine the fullness of the cartridge bladder 776 will turn off the ultrafiltrate supplying micropump 776 and provide a signal to the user that the cartridge needs emptying. The fluid bladder or cartridge 778 may contain an absorbent material (not specifically shown) for absorbing fluid presented to the bladder 778. The absorbent material may be a cotton, polymer, sponge, compressed material, powder, jell or other material that absorbs fluid and/or limits sloshing in the bladder or cartridge. The bladder may be designed to expand as it fills. The bladder may press against a microswitch 780 (not specifically shown) when it is full thereby providing a signal to the microprocessor 714.

The fluid bladder or cartridge 778 may have a means for emptying the fluid bladder 782 thereon in the form of a cap, stopper, valve, removable inner bladder or otherwise.

Referring back to the blood circuit in FIG. 12, reservoir/micropump combinations 784 (piezo pumps, solenoid pumps, syringe pumps, etc.) can be connected to the output side of the blood circuit dialyzer 730, 727. One or more micropumps and fluid reservoirs 784 can be connected. Additional heparin, electrolytes, blood additives, drugs, vitamins or hormones can be added to the dialyzed blood returning to the patient's body. The reservoir/micropump combinations are monitored and controlled by the microcontroller and can be adjusted via the user controls 723, or instructions received via the communication device 725.

Exemplary embodiments of the wearable CRT device can provide therapy from a basic dialysis function to a more complex medical dialysis, ultrafiltration, and medicinal therapy to a patient.

As discussed, there continues to be a growing body of literature indicating that increasing dialysis time, being longer or more frequent dialysis treatments, may be associated with improved outcomes in the treatment of End Stage Renal Disease (ESRD) patients, both in terms of life quality as well as expected morbidity and mortality.

However, the implementation of such modalities of treatment is complicated because of the lack of readily available economic resources to pay for the increased time or more frequent dialysis treatments. Furthermore, even if the money to pay for more dialysis time or treatments was available, there is currently limited additional nursing or technician manpower to deliver much more additional care. In addition, construction of additional facilities would be necessary to accommodate all these additional needs. Given the budgetary constrains of health care budgets in most countries, the chances of any or all of these things occurring is slim. Furthermore, very few dialysis patients are suitable for home self-treatment on non-wearable dialysis devices.

Embodiments of the wearable CRRT device are generally worn on a belt or strap by the patient and can be used for continuous renal replacement therapy twenty-four hours a day, seven days a week. Such embodiments can deliver significantly higher doses of dialysis than the intermittent dosing commonly administered by dialysis facilities today, while at the same time achieving significant reductions in manpower utilization and other medical related costs.

Recently an embodiment of the invention was tested to assess the efficiency and viability of the inventions in a uremic pig model. The efficiency of the exemplary wearable CRRT device was evaluated by achieving the removal of urea, creatinine, potassium, phosphorus and ultrafiltrate in amounts that would normalize the volume status as well as the above chemistries in uremic humans if the device would be worn continuously. Furthermore, the efficiency of the device was tested by achieving dialysis doses that would be equal to or higher than those afforded by intermittent daily dialysis, as measured by creatinine clearance, urea clearance and weekly urea Kt/V.

The exemplary embodiment of the wearable CRRT device used in the test comprised a blood circuit and a dialysate circuit. The blood circuit and dialysate circuit flowed through a small dialyzer that utilized polysulfone hollow fibers. The dialyzing surface area of the dialyzer was about 0.2 meters. The blood circuit had a port for the continuous administration of heparin into the circuit prior to the dialyzer. Both the blood and dialysate were propelled through their requisite circuits via a double channel pulsatile pump powered by replaceable batteries. The dirty or spent dialysate that exited the dialyzer was circulated through a series of filter cartridges containing urease and sorbents similar to those described by Marantz and coworker and widely used in the well known REDY system. Ultrafiltrate was removed by the dialysate circuit via a valving structure. The removed ultrafiltrate was directed to and stored in a plastic bag that was periodically emptied after volume measurement. Sensors connected to a micropressure monitored various aspects of the exemplary device.

Six farm raised pigs each weighing approximately 150 lbs. were anesthetized and made uremic by surgical ligation of both ureters. Twenty-four to forty-eight hours later the animals were again anesthetized and a double lumen Mahurkar catheter was inserted in a jugular vein. The catheter was connected to the exemplary CRRT device and each animal was dialyzed for eight hours. At the end of the eight hours the animals were euphemized.

Blood samples were drawn from an arterial line inserted in the carotid artery and CBC, urea, creatinine, sodium, potassium, chloride, $CO_2$, phosphorus, calcium and magnesium were measured. The same chemistries were measured in the dialysate circuit at the input side of the dialyzer and at the exit side of each filter cartridge.

The results of the test experiment were as follows. There were no adverse events observed in the animals during the test experiments. The average blood flow rate in the blood circuit was 44 ml/min and the average dialysate flow rate was 73 ml/min. The results of the test experiments are summarized in Tables I and II.

TABLE 1

Amount of Fluid Removed (in ml.) from each Animal in Eight Hours

|  | Pig C (g) | Pig D (g) | Pig E (g) | Pig F (g) | Pig G (g) | Pig H (g) |
|---|---|---|---|---|---|---|
| 1 hr. | 400 | 100 | 100 | 100 | 150 | 180 |
| 2 hrs | 700 | 200 | 200 | 200 | 220 | 200 |
| 3 hrs |  | 300 | 200 | 300 | 380 | 350 |
| 4 hrs | 800 | 400 | 250 | 400 | 500 | 700 |
| 5 hrs |  | 500 | 300 | 500 | 600 | 710 |
| 6 hrs |  | 500 | 500 | 800 | 690 | 1410 |
| 7 hrs |  | 620 | 600 | 1000 | 700 | 1400 |
| 8 hrs |  | 800 | 1000 | 1150 | 800 | 1400 |
| Average | 100 | 100 | 124 | 144 | 100 | 175 |

TABLE II

Experimental Data Acquired from Six Pigs, Using the Exemplary CRRT Device

|  | Creatinine Clearance (mL/min) | Total Creatinine Removed (g) (8 hrs) | Urea Clearance (mL/min) | Total Urea Removed (g) (8 hrs) | Weekly std (Kt/V) Urea | Phosphorus (grams) (24 hrs) | Potassium (mmole) (24 hrs) |
|---|---|---|---|---|---|---|---|
| Pig C | 20.10 | 0.91 | 29.40 | 7.61 | 6.50 | 2.30 | 266.11 |
| Pig D | 21.10 | 0.76 | 26.80 | 5.75 | 6.20 | 2.60 | 259.91 |
| Pig E | 23.50 | 1.14 | 27.30 | 5.37 | 6.10 | 2.67 | 303.54 |

TABLE II-continued

Experimental Data Acquired from Six Pigs, Using the Exemplary CRRT Device

|  | Creatinine Clearance (mL/min) | Total Creatinine Removed (g) (8 hrs) | Urea Clearance (mL/min) | Total Urea Removed (g) (8 hrs) | Weekly std (Kt/V) Urea | Phosphorus (grams) (24 hrs) | Potassium (mmole) (24 hrs) |
|---|---|---|---|---|---|---|---|
| Pig F | 23.50 | 1.14 | 27.30 | 5.37 | 6.00 | 2.44 | 270.50 |
| Pig G | 22.30 | 0.95 | 25.70 | 6.46 | 5.20 | 2.41 | 236.97 |
| Pig H | 22.30 | 1.02 | 26.30 | 6.24 | 5.80 | 2.42 | 227.01 |
| Mean | 22.13 ± 1.34 | 0.99 ± 0.15 | 27.13 ± 1.27 | 6.13 ± 0.85 | 5.97 ± 0.44 | 2.47 ± 0.14 | 260.67 ± 27.05 |

The fluid volume removed was changed arbitrarily during the experiment from 0 to about 700 ml/hr. The limiting factor for the removal of larger amounts of fluid per hour was a progressive decrease in blood flow in the dialyzer as the rate of fluid removal was increased. The blood flow normalized immediately as the rate of ultrafiltration (fluid removal) was decreased. There were no difficulties however in maintaining a fluid removal of 100 ml/hr. The amounts of urea, creatinine, potassium and phosphorus are further shown in FIGS. 13A through 13E. The amounts of potassium and phosphorous removed are expressed per twenty-four hours of treatment. The daily removal of potassium was 260.67±27.05 mmol/24 hrs. The daily removal of phosphorus was 2.47±0.14 gr/24 hours. The average creatinine clearance obtained with this exemplary embodiment was 22.13±1.34 ml/min. The average urea clearance was 27.13±1.27 ml/min and the weekly urea Kt/V was 5.97±0.44.

The lack of complications in the test experiments implies that the exemplary wearable CRRT device may be operated with the potential of no complications. The exemplary experimental wearable CRRT device has not displayed any complications differing from complications associated with existing large scale dialysis machines presently in use in the industry. The relatively low flow rates of the blood circuit and dialysate circuit help mitigate various complications found in some dialysis systems. Modifications can be made to the experimental exemplary CRRT device to allow an increase in the blood flow to range from about 50 to 120 ml/min. The modifications include at least one of increasing the size of the dialyzer, increasing the flow of the dual pump, and adjusting the transmission, gearing and valving of the pump.

The capacity of an exemplary wearable CRRT device to remove fluid steadily from the vascular space in amounts similar to the volume of fluids removed physiologically by normal kidney gives a treating physician the ability to keep a patient euvolemic, regardless of the amount of fluid the patient ingests. Further, the elimination of excess fluid may also result in better control of a patient's hypertension. The sodium concentration in the extracted ultrafiltrate is roughly equal to the sodium concentration of the patient's plasma. Thus, removal of about 0.5 to 3 liters of ultrafiltrate, via an exemplary CRRT device, a day will result in removal of about 10 to 20 grams of salt per day. Removal of sodium from a patient via an embodiment of the invention may contribute to better control of a patient's hypertension, and also result in liberalizing salt intake for ESRD patients. Thereby, perhaps improving a patient's quality of life by increasing the variety of foods a patient can eat. Furthermore, eating a variety of foods may result in improved nutrition for the patient.

Also, the amounts of potassium and phosphorus removed from a patient's blood by an exemplary wearable CRRT device further helps eliminate restrictions on oral intake of both the elements, and the elimination of a need for oral phosphate binders.

The experimental results indicate that the amount of creatinine and urea removed, as well as the high dialysis dose, expressed in both clearances and weekly urea Kt/V would make it feasible to achieve all the benefits of presently provided intermittent daily dialysis doses. The experiment, at the same time, proved a potential for decreasing the use of medical manpower and other costs associated with chronic dialysis.

Many variations and embodiments of the above-described invention are possible. Although only certain embodiments of the invention have been illustrated in the accompanying drawings and described in the foregoing Detailed Description, it will be understood that the invention is not limited to the embodiments disclosed, but is capable of additional rearrangements, modifications and substitutions without departing from the invention as set forth and defined by the following claims. Accordingly, it should be understood that the scope of the present invention encompasses all such arrangements and is solely limited by the claims as follows:

What is claimed is:

1. A continuous renal replacement therapy (CRRT) device comprising:
   means for enabling a patient to wear the entire CRRT device;
   a battery powered microcontroller;
   a blood circuit including a blood inlet tube for receiving blood from a patient, the blood circuit including:
      a first, battery powered pump channel, controlled by the microcontroller for pumping blood in a pulsatile manner through the blood circuit;
      a first micropump for pumping an anticoagulant into the blood circuit;
      a dialyzer for receiving blood pumped by the first pump channel;
      a pressure transducer for providing a blood circuit pressure signal to the microcontroller;
      an outlet port for allowing blood to go back into the patient after being received by the dialyzer; and
   a dialysate circuit for circulating dialysate through the dialyzer and for removing contaminants from the circulating dialysate, the dialysate circuit comprising:
      a second, battery powered pump channel, controlled by the microcontroller, for pumping dialysate in a pulsatile manner at a flow rate between 40 ml/min and 100 ml/min through the dialysate circuit;
      a filter section for reacting with predetermined substances in the dialysate in order to refresh the dialysate for continued usage in the dialysate circuit;

a sensor, attached to the dialysate circuit, for providing a signal to the microcontroller indicating that the filter section requires maintenance;

a degasser, attached to the dialysate circuit, for removing gas from the dialysate circuit; and wherein the microcontroller, blood circuit and dialysate circuit are operably interconnected to provide continuous renal replacement therapy while the CRRT device is worn by a patient.

2. The CRRT device of claim 1, wherein the first pump channel and the second pump channel each pump a predetermined number of degrees out of phase.

3. The CRRT device of claim 1 wherein the device utilizes less than about 1 liter of dialysate to provide continuous renal replacement therapy to a patient for a 24 hour period.

4. The CRRT device of claim 1 wherein the filter section comprises a replaceable cartridge adapted to be replaced by the patient.

5. The CRRT device of claim 1, wherein the blood circuit further comprises an additional micropump for infusing at least one of electrolytes, blood additives, drugs, vitamins and hormones into the blood.

6. The CRRT device of claim 1 further comprising a fluid container operatively connected to the dialysate circuit for removing ultrafiltrate and dialysate from the dialysate circuit.

7. The CRRT device of claim 6 further comprising a sensor operatively connected to the fluid container, the sensor transmitting a signal indicating a fluid volume in the container.

8. A wearable, continuous renal replacement therapy (CRRT) device comprising:

a battery powered microcontroller;

a battery powered, dual channel pulsatile pump, controlled by the microcontroller, the dual channel pulsatile pump including a motor, a first pump channel and a second pump channel;

a blood circuit comprising:

a blood inlet tube for receiving blood from a patient wherein the first pump channel pumps blood in a pulsatile manner through the blood circuit;

a first micropump for pumping an anticoagulant into the blood circuit, the micropump being controlled by the microcontroller;

a dialyzer for receiving blood pumped by the first pump channel;

a first pressure transducer for providing a first blood circuit pressure signal to the microcontroller;

an outlet port for allowing blood to go back into the patient after being received by the dialyzer;

a dialysate circuit for circulating dialysate through the dialyzer and for removing contaminants from the circulating dialysate, wherein the second pump channel pumps dialysate at a flow rate between 40 ml/min and 100 ml/min in a pulsatile manner through the circuit, the dialysate circuit comprising:

a filter section for reacting with predetermined substances in the dialysate in order to refresh the dialysate for continued usage in the dialysate circuit;

a sensor, attached to the dialysate circuit, providing a signal to the microcontroller indicating that the filter section requires maintenance;

an alarm operatively connected to the microcontroller, the alarm indicating that the continuous renal replacement therapy (CRRT) device requires maintenance; and wherein the microcontroller, dual channel pulsatile pump, blood circuit, dialysate circuit are operably interconnected to provide continuous renal replacement therapy while the CRRT device is worn by a patient.

9. The CRRT device of claim 8 wherein the alarm is one of an audio, visual or physical alarm device.

10. The CRRT device of claim 8, further comprising an anticoagulant reservoir in fluid communication with the first micropump and a fluid sensor associated with the anticoagulant reservoir, the fluid sensor providing a signal to the microcontroller when the volume of anticoagulant in the anticoagulant reservoir is below a predetermined volume.

11. The CRRT device of claim 8 wherein the circulating volume of dialysate in the dialysate circuit is less than about one liter.

12. The CRRT device of claim 8 wherein the first pressure transmitter is connected to the blood circuit before the pump, the CRRT device further comprising a second pressure transducer connected to the blood circuit after the pump for providing a second blood circuit pressure signal to the microcontroller for determining the blood circuit pressure differential across the pump.

13. The CRRT device of claim 12 further comprising a third pressure transducer connected to the blood circuit after the dialyzer for providing a third blood circuit pressure signal to the microcontroller for determining the blood circuit pressure differential across the dialyzer.

14. The CRRT device of claim 8 further comprising a fourth pressure transducer connected to the dialysate circuit after the pump for providing a first dialysate circuit pressure signal to the microcontroller.

15. The CRRT device of claim 14 further comprising a fifth pressure transducer connected to the dialysate circuit after the dialyzer for sending a second dialysate circuit pressure signal to the microcontroller for determining a dialysate circuit pressure differential across the dialyzer.

16. A wearable, continuous renal replacement therapy (CRRT) device comprising:

a battery powered microcontroller;

first and second pump channels for pumping blood and dialysate, respectively, in a pulsatile manner wherein the first and second pump channels each pump a predetermined number of degrees out of phase;

a blood circuit comprising:

a blood inlet tube for receiving blood from a patient wherein the first pump channel pumps blood in a pulsatile manner through the blood circuit;

a first micropump for pumping an anticoagulant into the blood circuit; a dialyzer receiving blood pumped by the first pump channel;

a second micropump for adding at least one of electrolytes, blood additives, drugs, vitamins and hormones to the blood prior to the blood returning to the patient;

a pressure transducer for providing a blood circuit pressure signal to the microcontroller;

an outlet port for allowing blood to go back into the patient after being received by the dialyzer; and a dialysate circuit for circulating dialysate through the dialyzer and for removing contaminants from the circulating dialysate wherein the second pump channel pumps dialysate at a flow rate between 40 ml/min and 100 ml/min through the dialysate circuit, the dialysate circuit comprising:

a filter section for refreshing the dialysate for continued usage in the dialysate circuit, the filter section including a plurality of discrete filters;

a sensor, attached to the dialysate circuit, providing a signal to the microprocessor indicating that the filter section requires maintenance;

a degasser, attached to the dialysate circuit, for removing gas from the dialysate circuit; and wherein the microcontroller, first and second pump channels, blood circuit, and dialysate circuit are operably interconnected to provide continuous renal replacement therapy while worn by a patient.

17. The CRRT device of claim 16 further comprising an alarm and wherein the sensor senses ammonia in the dialysate and transmits a signal to activate the alarm when a predetermined amount of ammonia is detected in the dialysate.

18. The CRRT device of claim 16 further comprising an alarm and wherein the sensor senses the pH of the dialysate and transmits a signal to activate the alarm when the pH of the dialysate reaches a predetermined value.

19. The CRRT device of claim 16 further comprising an alarm and wherein the sensor senses the conductivity of the dialysate and transmits a signal to activate the alarm when the conductivity of the dialysate reaches a predetermined value.

20. The CRRT of claim 16 further comprising an alarm and a liquid detector and wherein the moisture sensor transmits a signal to activate the alarm when a liquid is detected in the CRRT device outside of the blood or dialysate circuits.

* * * * *